US012303386B2

(12) United States Patent
Fahim et al.

(10) Patent No.: US 12,303,386 B2
(45) Date of Patent: May 20, 2025

(54) STENT ASSEMBLY FOR USE IN PROSTHETIC HEART VALVES

(71) Applicant: St. Jude Medical, Cardiology Division, Inc., St. Paul, MN (US)

(72) Inventors: Mina S. Fahim, Shoreview, MN (US); Peter N. Braido, Wyoming, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 484 days.

(21) Appl. No.: 17/813,790

(22) Filed: Jul. 20, 2022

(65) Prior Publication Data

US 2022/0354640 A1    Nov. 10, 2022

Related U.S. Application Data

(63) Continuation of application No. 16/571,688, filed on Sep. 16, 2019, now Pat. No. 11,413,142, which is a
(Continued)

(51) Int. Cl.
*A61F 2/24* (2006.01)
*A61F 2/844* (2013.01)
*A61F 2/90* (2013.01)

(52) U.S. Cl.
CPC .......... *A61F 2/2418* (2013.01); *A61F 2/2412* (2013.01); *A61F 2/844* (2013.01);
(Continued)

(58) Field of Classification Search
CPC ...... A61F 2/2412; A61F 2/2418; A61F 2/844; A61F 2/90; A61F 2250/0069
See application file for complete search history.

(56) References Cited

U.S. PATENT DOCUMENTS 3,657,744 A    4/1972    Ersek
4,275,469 A    6/1981    Gabbay
(Continued)

FOREIGN PATENT DOCUMENTS

DE    19857887 B4    5/2005
DE    10121210 B4    11/2005
(Continued)

OTHER PUBLICATIONS

"Transluminal Implantation of Artificial Heart Valves", Andersen, H. R., et al., European Heart Journal, vol. 13, No. 5, May 1992, pp. 704-708.
(Continued)

*Primary Examiner* — Brian A Dukert
(74) *Attorney, Agent, or Firm* — SLEMAN & LUND LLP

(57) ABSTRACT

A prosthetic heart valve having a cuff attached to a stent provides a seal for preventing paravalvular leakage. The cuff may be constructed from known sealing materials to fill in and around paravalvular leakage gaps, while continuously collapsing down into a low profile volume within the stent. The cuff is coupled circumferentially about the stent by members which may be in the nature of dimension and/or shape memory material having a tensioned and relaxed state. The members may be in the form of elongated elastic members or coiled members. When in the tensioned state, the cuff is located within the stent volume to provide a low profile prosthetic heart valve. Upon relaxing of the members, the cuff is pulled over the abluminal surface of the stent to form a cuff seal circumscribing the stent for preventing paravalvular leakage.

17 Claims, 9 Drawing Sheets

Related U.S. Application Data continuation of application No. 15/649,964, filed on Jul. 14, 2017, now Pat. No. 10,420,641, which is a continuation of application No. 14/713,399, filed on May 15, 2015, now Pat. No. 9,757,230.

(60) Provisional application No. 61/994,187, filed on May 16, 2014.

(52) U.S. Cl.
CPC ........ *A61F 2/90* (2013.01); *A61F 2210/0014* (2013.01); *A61F 2230/0065* (2013.01); *A61F 2250/0069* (2013.01)

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann |
| 4,922,905 A | 5/1990 | Strecker |
| 4,994,077 A | 2/1991 | Dobben |
| 5,411,552 A | 5/1995 | Andersen |
| 5,415,664 A | 5/1995 | Pinchuk |
| 5,480,423 A | 1/1996 | Ravenscroft |
| 5,843,167 A | 12/1998 | Dwyer |
| 5,855,601 A | 1/1999 | Bessler |
| 5,935,163 A | 8/1999 | Gabbay |
| 5,961,549 A | 10/1999 | Nguyen |
| 6,045,576 A | 4/2000 | Starr |
| 6,077,297 A | 6/2000 | Robinson |
| 6,083,257 A | 7/2000 | Taylor |
| 6,090,140 A | 7/2000 | Gabbay |
| 6,214,036 B1 | 4/2001 | Letendre |
| 6,264,691 B1 | 7/2001 | Gabbay |
| 6,267,783 B1 | 7/2001 | Letendre |
| 6,368,348 B1 | 4/2002 | Gabbay |
| 6,419,695 B1 | 7/2002 | Gabbay |
| 6,458,153 B1 | 10/2002 | Bailey |
| 6,468,660 B2 | 10/2002 | Ogle |
| 6,488,702 B1 | 12/2002 | Besselink |
| 6,517,576 B2 | 2/2003 | Gabbay |
| 6,533,810 B2 | 3/2003 | Hankh |
| 6,582,464 B2 | 6/2003 | Gabbay |
| 6,610,088 B1 | 8/2003 | Gabbay |
| 6,623,518 B2 | 9/2003 | Thompson |
| 6,652,578 B2 | 11/2003 | Bailey |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser |
| 6,783,556 B1 | 8/2004 | Gabbay |
| 6,790,230 B2 | 9/2004 | Beyersdorf |
| 6,814,746 B2 | 11/2004 | Thompson |
| 6,830,584 B1 | 12/2004 | Seguin |
| 6,869,444 B2 | 3/2005 | Gabbay |
| 6,893,460 B2 | 5/2005 | Spenser |
| 6,908,481 B2 | 6/2005 | Cribier |
| 6,951,573 B1 | 10/2005 | Dilling |
| 7,018,406 B2 | 3/2006 | Seguin |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz |
| 7,247,167 B2 | 7/2007 | Gabbay |
| 7,267,686 B2 | 9/2007 | DiMatteo |
| 7,276,078 B2 | 10/2007 | Spenser |
| 7,311,730 B2 | 12/2007 | Gabbay |
| 7,320,704 B2 | 1/2008 | Lashinski |
| 7,329,278 B2 | 2/2008 | Seguin |
| 7,374,573 B2 | 5/2008 | Gabbay |
| 7,381,218 B2 | 6/2008 | Schreck |
| 7,381,219 B2 | 6/2008 | Salahieh |
| 7,452,371 B2 | 11/2008 | Pavcnik |
| 7,510,572 B2 | 3/2009 | Gabbay |
| 7,510,575 B2 | 3/2009 | Spenser |
| 7,524,331 B2 | 4/2009 | Birdsall |
| 7,534,261 B2 | 5/2009 | Friedman |
| RE40,816 E | 6/2009 | Taylor |
| 7,585,321 B2 | 9/2009 | Cribier |
| 7,628,805 B2 | 12/2009 | Spenser |
| 7,682,390 B2 | 3/2010 | Seguin |
| 7,708,775 B2 | 5/2010 | Rowe |
| 7,731,742 B2 | 6/2010 | Schlick |
| 7,748,389 B2 | 7/2010 | Salahieh |
| 7,780,725 B2 | 8/2010 | Haug |
| 7,799,069 B2 | 9/2010 | Bailey |
| 7,803,185 B2 | 9/2010 | Gabbay |
| 7,824,442 B2 | 11/2010 | Salahieh |
| 7,837,727 B2 | 11/2010 | Goetz |
| 7,846,203 B2 | 12/2010 | Cribier |
| 7,846,204 B2 | 12/2010 | Letac |
| 7,857,845 B2 | 12/2010 | Stacchino |
| 7,892,281 B2 | 2/2011 | Seguin |
| 7,914,569 B2 | 3/2011 | Nguyen |
| 7,959,666 B2 | 6/2011 | Salahieh |
| 7,959,672 B2 | 6/2011 | Salahieh |
| 7,972,378 B2 | 7/2011 | Tabor |
| 7,988,724 B2 | 8/2011 | Salahieh |
| 7,993,394 B2 | 8/2011 | Hariton |
| 8,016,877 B2 | 9/2011 | Seguin |
| D648,854 S | 11/2011 | Braido |
| 8,048,153 B2 | 11/2011 | Salahieh |
| 8,052,741 B2 | 11/2011 | Bruszewski |
| 8,052,749 B2 | 11/2011 | Salahieh |
| 8,052,750 B2 | 11/2011 | Tuval |
| 8,062,355 B2 | 11/2011 | Figulla |
| 8,075,611 B2 | 12/2011 | Millwee |
| D652,926 S | 1/2012 | Braido |
| D652,927 S | 1/2012 | Braido |
| D653,341 S | 1/2012 | Braido |
| D653,342 S | 1/2012 | Braido |
| D653,343 S | 1/2012 | Ness |
| D654,169 S | 2/2012 | Braido |
| D654,170 S | 2/2012 | Braido |
| 8,137,398 B2 | 3/2012 | Tuval |
| 8,142,497 B2 | 3/2012 | Friedman |
| D660,432 S | 5/2012 | Braido |
| D660,433 S | 5/2012 | Braido |
| D660,967 S | 5/2012 | Braido |
| 8,182,528 B2 | 5/2012 | Salahieh |
| 8,221,493 B2 | 7/2012 | Boyle |
| 8,230,717 B2 | 7/2012 | Matonick |
| 8,231,670 B2 | 7/2012 | Salahieh |
| 8,252,051 B2 | 8/2012 | Chau |
| 8,308,798 B2 | 11/2012 | Pintor |
| 8,313,525 B2 | 11/2012 | Tuval |
| 8,323,335 B2 | 12/2012 | Rowe |
| 8,323,336 B2 | 12/2012 | Hill |
| 8,343,213 B2 | 1/2013 | Salahieh |
| 8,348,995 B2 | 1/2013 | Tuval |
| 8,348,996 B2 | 1/2013 | Tuval |
| 8,348,998 B2 | 1/2013 | Pintor |
| 8,366,769 B2 | 2/2013 | Huynh |
| 8,403,983 B2 | 3/2013 | Quadri |
| 8,408,214 B2 | 4/2013 | Spenser |
| 8,414,643 B2 | 4/2013 | Tuval |
| 8,425,593 B2 | 4/2013 | Braido |
| 8,449,599 B2 | 5/2013 | Chau |
| 8,449,604 B2 | 5/2013 | Moaddeb |
| D684,692 S | 6/2013 | Braido |
| 8,454,686 B2 | 6/2013 | Alkhatib |
| 8,500,798 B2 | 8/2013 | Rowe |
| 8,568,474 B2 | 10/2013 | Yeung |
| 8,579,962 B2 | 11/2013 | Salahieh |
| 8,579,966 B2 | 11/2013 | Seguin |
| 8,585,755 B2 | 11/2013 | Chau |
| 8,591,575 B2 | 11/2013 | Cribier |
| 8,597,349 B2 | 12/2013 | Alkhatib |
| 8,603,159 B2 | 12/2013 | Seguin |
| 8,603,160 B2 | 12/2013 | Salahieh |
| 8,613,765 B2 | 12/2013 | Bonhoeffer |
| 8,623,074 B2 | 1/2014 | Ryan |
| 8,652,204 B2 | 2/2014 | Quill |

(56) References Cited

U.S. PATENT DOCUMENTS

| | | |
|---|---|---|
| 8,663,322 B2 | 3/2014 | Olli |
| 8,668,733 B2 | 3/2014 | Haug |
| 8,685,080 B2 | 4/2014 | White |
| 8,728,154 B2 | 5/2014 | Alkhatib |
| 8,747,459 B2 | 6/2014 | Nguyen |
| 8,764,820 B2 | 7/2014 | Dehdashtian |
| 8,795,357 B2 | 8/2014 | Yohanan |
| 8,801,776 B2 | 8/2014 | House |
| 8,808,356 B2 | 8/2014 | Braido |
| 8,828,078 B2 | 9/2014 | Salahieh |
| 8,834,563 B2 | 9/2014 | Righini |
| 8,840,661 B2 | 9/2014 | Manasse |
| 8,840,663 B2 | 9/2014 | Salahieh |
| 8,876,894 B2 | 11/2014 | Tuval |
| 8,876,895 B2 | 11/2014 | Tuval |
| 8,940,040 B2 | 1/2015 | Shahriari |
| 8,945,209 B2 | 2/2015 | Bonyuet |
| 8,961,595 B2 | 2/2015 | Alkhatib |
| 8,974,523 B2 | 3/2015 | Thill |
| 8,974,524 B2 | 3/2015 | Yeung |
| 9,480,559 B2 * | 11/2016 | Vidlund .............. A61L 27/3625 |
| 10,195,025 B2 | 2/2019 | Levi |
| 2002/0036220 A1 | 3/2002 | Gabbay |
| 2003/0023303 A1 | 1/2003 | Palmaz |
| 2003/0050694 A1 | 3/2003 | Yang |
| 2003/0130726 A1 | 7/2003 | Thorpe |
| 2004/0049262 A1 | 3/2004 | Obermiller |
| 2004/0093075 A1 | 5/2004 | Kuehne |
| 2004/0111111 A1 | 6/2004 | Lin |
| 2004/0210304 A1 | 10/2004 | Seguin |
| 2004/0260389 A1 | 12/2004 | Case |
| 2005/0096726 A1 | 5/2005 | Sequin |
| 2005/0137682 A1 | 6/2005 | Justino |
| 2005/0137695 A1 | 6/2005 | Salahieh |
| 2005/0137697 A1 | 6/2005 | Salahieh |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0058872 A1 | 3/2006 | Salahieh |
| 2006/0074484 A1 | 4/2006 | Huber |
| 2006/0122692 A1 | 6/2006 | Gilad |
| 2006/0149360 A1 | 7/2006 | Schwammenthal |
| 2006/0161249 A1 | 7/2006 | Realyvasquez |
| 2006/0173532 A1 | 8/2006 | Flagle |
| 2006/0178740 A1 | 8/2006 | Stacchino |
| 2006/0195180 A1 | 8/2006 | Kheradvar |
| 2006/0206202 A1 | 9/2006 | Bonhoeffer |
| 2006/0241744 A1 | 10/2006 | Beith |
| 2006/0259120 A1 | 11/2006 | Vongphakdy |
| 2006/0259137 A1 | 11/2006 | Artof |
| 2006/0265056 A1 | 11/2006 | Nguyen |
| 2006/0276813 A1 | 12/2006 | Greenberg |
| 2006/0276874 A1 | 12/2006 | Wilson |
| 2007/0010876 A1 | 1/2007 | Salahieh |
| 2007/0027534 A1 | 2/2007 | Bergheim |
| 2007/0043435 A1 | 2/2007 | Seguin |
| 2007/0055358 A1 | 3/2007 | Krolik |
| 2007/0067029 A1 | 3/2007 | Gabbay |
| 2007/0093890 A1 | 4/2007 | Eliasen |
| 2007/0100435 A1 | 5/2007 | Case |
| 2007/0118210 A1 | 5/2007 | Pinchuk |
| 2007/0198097 A1 | 8/2007 | Zegdi |
| 2007/0213813 A1 | 9/2007 | Von Segesser |
| 2007/0233228 A1 | 10/2007 | Eberhardt |
| 2007/0244545 A1 | 10/2007 | Birdsall |
| 2007/0244552 A1 | 10/2007 | Salahieh |
| 2007/0288087 A1 | 12/2007 | Fearnot |
| 2008/0021552 A1 | 1/2008 | Gabbay |
| 2008/0039934 A1 | 2/2008 | Styrc |
| 2008/0071369 A1 | 3/2008 | Tuval |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey |
| 2008/0140189 A1 | 6/2008 | Nguyen |
| 2008/0147183 A1 | 6/2008 | Styrc |
| 2008/0154355 A1 | 6/2008 | Benichou |
| 2008/0154356 A1 | 6/2008 | Obermiller |
| 2008/0243245 A1 | 10/2008 | Thambar |
| 2008/0255662 A1 | 10/2008 | Stacchino |
| 2008/0262602 A1 | 10/2008 | Wilk |
| 2008/0269879 A1 | 10/2008 | Sathe |
| 2009/0099653 A1 | 4/2009 | Suri |
| 2009/0112309 A1 | 4/2009 | Jaramillo |
| 2009/0138079 A1 | 5/2009 | Tuval |
| 2009/0276027 A1 | 11/2009 | Glynn |
| 2010/0004740 A1 | 1/2010 | Seguin |
| 2010/0036484 A1 | 2/2010 | Hariton |
| 2010/0049306 A1 | 2/2010 | House |
| 2010/0087907 A1 | 4/2010 | Omar |
| 2010/0131055 A1 | 5/2010 | Case |
| 2010/0168778 A1 | 7/2010 | Braido |
| 2010/0168839 A1 | 7/2010 | Braido |
| 2010/0168844 A1 | 7/2010 | Toomes |
| 2010/0185277 A1 | 7/2010 | Braido |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau |
| 2010/0234940 A1 | 9/2010 | Dolan |
| 2010/0249911 A1 | 9/2010 | Alkhatib |
| 2010/0249923 A1 | 9/2010 | Alkhatib |
| 2010/0286768 A1 | 11/2010 | Alkhatib |
| 2010/0298931 A1 | 11/2010 | Quadri |
| 2011/0029072 A1 | 2/2011 | Gabbay |
| 2011/0054466 A1 | 3/2011 | Rothstein |
| 2011/0098800 A1 | 4/2011 | Braido |
| 2011/0098802 A1 | 4/2011 | Braido |
| 2011/0137397 A1 | 6/2011 | Chau |
| 2011/0172765 A1 | 7/2011 | Nguyen |
| 2011/0208283 A1 | 8/2011 | Rust |
| 2011/0264206 A1 | 10/2011 | Tabor |
| 2012/0035722 A1 | 2/2012 | Tuval |
| 2012/0078347 A1 | 3/2012 | Braido |
| 2012/0101572 A1 | 4/2012 | Kovalsky |
| 2012/0123529 A1 | 5/2012 | Levi |
| 2012/0303116 A1 | 11/2012 | Gorman, III |
| 2013/0274873 A1 | 10/2013 | Delaloye |
| 2013/0331929 A1 * | 12/2013 | Mitra ................... A61F 2/2418 623/2.11 |
| 2014/0121763 A1 | 5/2014 | Duffy |
| 2014/0155997 A1 | 6/2014 | Braido |
| 2014/0214159 A1 | 7/2014 | Robert |
| 2014/0228946 A1 | 8/2014 | Chau |
| 2014/0277417 A1 | 9/2014 | Schraut |
| 2014/0277419 A1 | 9/2014 | Garde |
| 2014/0303719 A1 | 10/2014 | Cox |
| 2014/0324164 A1 | 10/2014 | Gross |
| 2014/0343671 A1 | 11/2014 | Yohanan |
| 2014/0350668 A1 | 11/2014 | Delaloye |
| 2014/0350669 A1 | 11/2014 | Gillespie |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1926455 A2 | 6/2008 |
| EP | 2537487 A1 | 12/2012 |
| EP | 1758523 B1 | 9/2013 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 2001028459 A1 | 4/2001 |
| WO | 0149213 A2 | 7/2001 |
| WO | 0156500 A2 | 8/2001 |

(56) References Cited

FOREIGN PATENT DOCUMENTS

| WO | 2001054625 | A1 | 8/2001 |
|---|---|---|---|
| WO | 2001076510 | A2 | 10/2001 |
| WO | 2002036048 | A1 | 5/2002 |
| WO | 0247575 | A2 | 6/2002 |
| WO | 02067782 | A2 | 9/2002 |
| WO | 2003047468 | A1 | 6/2003 |
| WO | 2005070343 | A1 | 8/2005 |
| WO | 2006073626 | A2 | 7/2006 |
| WO | 2007071436 | A2 | 6/2007 |
| WO | 2008070797 | A2 | 6/2008 |
| WO | 2010008548 | A2 | 1/2010 |
| WO | 2010008549 | A1 | 1/2010 |
| WO | 2010096176 | A1 | 8/2010 |
| WO | 2010098857 | A1 | 9/2010 |
| WO | 2013028387 | A2 | 2/2013 |
| WO | 2013059743 | A1 | 4/2013 |
| WO | 2014164149 | A1 | 10/2014 |
| WO | 2015077274 | A1 | 5/2015 |

OTHER PUBLICATIONS

Andersen, Henning Rud, Transluminal Catheter Implanted Prosthetic Heart Valves, International Journal of Angiology 7:102-106 (1998).

Buellesfeld, et al., "Treatment of paravalvular leaks through inverventional techniques," Multimed Man Cardiothorac Surg., Department of Cardiology, Ben University Hospital, pp. 1-8, Jan. 2011.

De Cicco, et al., "Aortic Valve Periprosthetic Leakage: Anatomic Observations and Surgical Results", The Annals of Thoracic Surgery, vol. 79, No. 5, May 2005, pp. 1480-1485.

Dewey, et al., "Transapical Aortic Valve Implantation: An Animal Feasibility Study", The Annals of Thoracic Surgery, vol. 82, No. 1, Jul. 2006, pp. 110-116.

Gössl et al., "Percutaneous Treatment of Aortic and Mitral Valve Paravalvular Regurgitation", Current Cardiology Reports, vol. 15, No. 8, Aug. 2013, pp. 1-8.

Heat Advisor, "Heart Repairs Without Surgery: Minimally Invasive Procedures Aim to Correct Valve Leakage", Technology Frontier, Sep. 2004, pp. 4-5.

Hijazi et al., Transcatheter Valve Repair, CRC Press, Jan. 2006, pp. 165-186.

Hourihan, et al., "Transcatheter Umbrella Closure of Valvular and Paravalvular Leaks," Journal of the American College of Cardiology, vol. 20, No. 6, pp. 1371-1377, Nov. 1992.

Huber, et al., "Direct-Access Valve Replacement: A Novel Approach for Off-Pump Valve Implantation Using Valved Stents", Journal of the American College of Cardiology, vol. 46, No. 2, Jul. 2005, pp. 366-370.

International Search Report and Written Opinion for Application No. PCT/US2015/030945 dated Jul. 31, 2015.

Knudsen LL, Andersen HR, Hasenkam JM. Catheter-Implanted Prosthetic Heart Valves: Transluminal catheter Implantation of a new expandable artificial heart valve in the descending thoracic aorta in isolated vessels and closed chest pigs. The International Journal of Artificial Organs. May 1993; 16(5):253-62.

M.J. Mack, "Minimally invasive cardiac surgery", Surgical Endoscopy, 20:S488-S492, DOI: 10.1007/s00464-006-0110-8 Presented Mar. 23, 2006.

Mack, "Minimally invasive cardiac surgery", Surgical Endoscopy, 2006, 20:S488-S492, DOI: 10.1007/s00464-006-0110-8, presented Apr. 24, 2006.

Moazami et al., "Transluminal Aortic Valve Placement: A Feasibility Study With a Newly designed Collapsible Aortic Valve.", ASAIO Journal, (19960900), vol. 42, pp. M381-M385, XP000683605.

Quaden et al., "Percutaneous aortic valve replacement: resection before implantation", European J. of Cardio-thoracic Surgery, vol. 27, Issue 5, pp. 836-840, May 2005.

Rodriguez et al., "Guidance of Treatment of Pehvalvular Prosthetic Leaks", Current Cardiology Reports, vol. 16, No. 1, Nov. 2013, pp. 1-6.

Rohde, et al., "Resection of Calcified Aortic Heart Leaflets In Vitro by Q-Switched 2 pm Microsecond Laser Radiation", Journal of Cardiac Surgery, 30(2): 157-62. Feb. 2015.

Samuel V. Lichtenstein et al., Transapical Transcatheter Aortic Valve Implantation in Humans, Circulation, Jul. 2006, pp. 591-596, vol. 114.

Samuel V. Lichtenstein, "Closed heart surgery: Back to the future", The Journal of Thoracic and Cardiovascular Surgery, vol. 131, No. 5, pp. 941-943, May 2006.

Swiatkiewicz, et al., "Percutaneous closure of mitral perivalvular leak," Kardiologia Polska, vol. 67, No. 7, pp. 762-764, Jul. 2009.

Th. Walther et al., "Transapical Approach for Sutureless Stent-Fixed Aortic Valve Implantation: Experimental Results", European Journal of Cardio-Thoracic Surgery, vol. 29, No. 5, May 2006, pp. 703-708.

Webb et al., "Percutaneous Aortic Valve Implantation Retrograde From the Femoral Artery", Circulation, published online Feb. 2006, pp. 842-850, vol. 113, American Heart Association, Dallas, TX, USA.

Zegdi, Rachid, MD, PhD et al., "Is It Reasonable to Treat All Calcified Stenotic Aortic Valves With a Valved Stent?" 579-584, J. of the American College of Cardiology, vol. 51. No. 5, Feb. 5, 2008.

\* cited by examiner

STENT ASSEMBLY FOR USE IN PROSTHETIC HEART VALVES

CROSS-REFERENCE TO RELATED APPLICATIONS

The present application is a continuation of U.S. patent application Ser. No. 16/571,688, filed Sep. 16, 2019, which is a continuation of U.S. Pat. No. 10,420,641, filed Jul. 14, 2017, which is a continuation of U.S. Pat. No. 9,757,230, filed May 15, 2015, which claims the benefit of the filing date of U.S. Provisional Patent Application No. 61/994,187, filed May 16, 2014, the disclosure of which is hereby incorporated herein by reference.

BACKGROUND OF THE DISCLOSURE

The present disclosure relates to a stent assembly for heart valve replacement and, in particular, to collapsible prosthetic heart valves. More particularly, the present disclosure relates to collapsible prosthetic transcatheter heart valves which minimize or reduce paravalvular leaks.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent and a balloon-expandable stent. To place such valves into a delivery apparatus and ultimately into a patient, the valve is first collapsed or crimped to reduce its circumferential size. It is therefore desirable that the valve have a low profile or volume to minimize the size of the delivery apparatus.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as a sheath covering the valve is withdrawn.

There is a need for improvements to prosthetic heart valves, and specifically, to collapsible prosthetic heart valves that would reduce the likelihood of paravalvular leakage due to gaps between the implanted prosthetic heart valve and patient tissue.

BRIEF SUMMARY OF THE DISCLOSURE

In one embodiment of the present disclosure there is described a stent assembly for use in a prosthetic heart valve for replacing a native valve. The prosthetic heart valve includes a stent having a luminal surface and an abluminal surface extending between a distal end and a proximal end thereof. A valve may be disposed within the stent. A cuff may be coupled to the stent having a first orientation and a second orientation. A plurality of members may be provided having a distal end coupled to the stent and a proximal end coupled to the cuff. The plurality of members has a first state when the cuff is arranged in the first orientation and a second state when the cuff is arranged in the second orientation.

In another embodiment of the present disclosure there is also described a stent assembly for use in a prosthetic heart valve for replacing a native valve. The prosthetic heart valve includes a stent having a proximal end and an abluminal surface. A valve may be disposed within the stent. A cuff may be coupled to the stent by a plurality of members having a relaxed state and a tensioned state for orienting at least a portion of the cuff at least partially disposed on the abluminal surface when the plurality of members are in a relaxed state.

In a further embodiment of the present disclosure there is also described a stent assembly for use in a prosthetic heart valve for replacing a native valve. The prosthetic heart valve includes a stent. A valve may be disposed within the stent. A cuff may be coupled to the stent having a first orientation and a second orientation. A plurality of members may be coupled between the stent and cuff. The members are configured to arrange the cuff between the first and second orientations, wherein the members remain coupled to the stent and cuff after replacement of the native valve.

In a further embodiment of the present disclosure there is also described a stent assembly for use in a prosthetic heart valve for replacing a native valve. The prosthetic heart valve includes a stent configured to have a collapsed condition and an expanded condition. The stent has a luminal surface and an abluminal surface extending between a distal end and a proximal end thereof. A valve assembly may be disposed within the stent. The valve assembly may include a plurality of leaflets and a cuff having a portion at least partially disposed on the luminal surface of the stent. At least a portion of the cuff has a first orientation extending outwardly of the proximal end of the stent or at least partially disposed on the abluminal surface of the stent and a second orientation with a portion of the cuff at least partially disposed on the abluminal surface of the stent. A plurality of elongated elastic members has a distal end coupled to the stent and a proximal end coupled to the cuff at circumferentially spaced apart locations. The plurality of elastic members has a tensioned state when the cuff is arranged in the first orientation and a relaxed state when the cuff is arranged in the second orientation.

In a further embodiment of the present disclosure there is also described a stent assembly for use in a prosthetic heart valve for replacing a native valve. The prosthetic heart valve includes a stent. A cuff may be coupled to the stent having a first orientation and a second orientation. A plurality of inverting members may be coupled between the stent and cuff. The members are configured to arrange the cuff between the first and second orientations, wherein the inverting members remain coupled to the stent and cuff after replacement of the native valve.

BRIEF DESCRIPTION OF THE DRAWINGS

Various embodiments of the presently disclosed stent assembly and prosthetic heart valves may be more fully understood with reference to the following detailed description when read with the accompanying drawings, in which.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. Like reference numbers refer to similar or identical elements throughout the disclosure.

Figure 1:
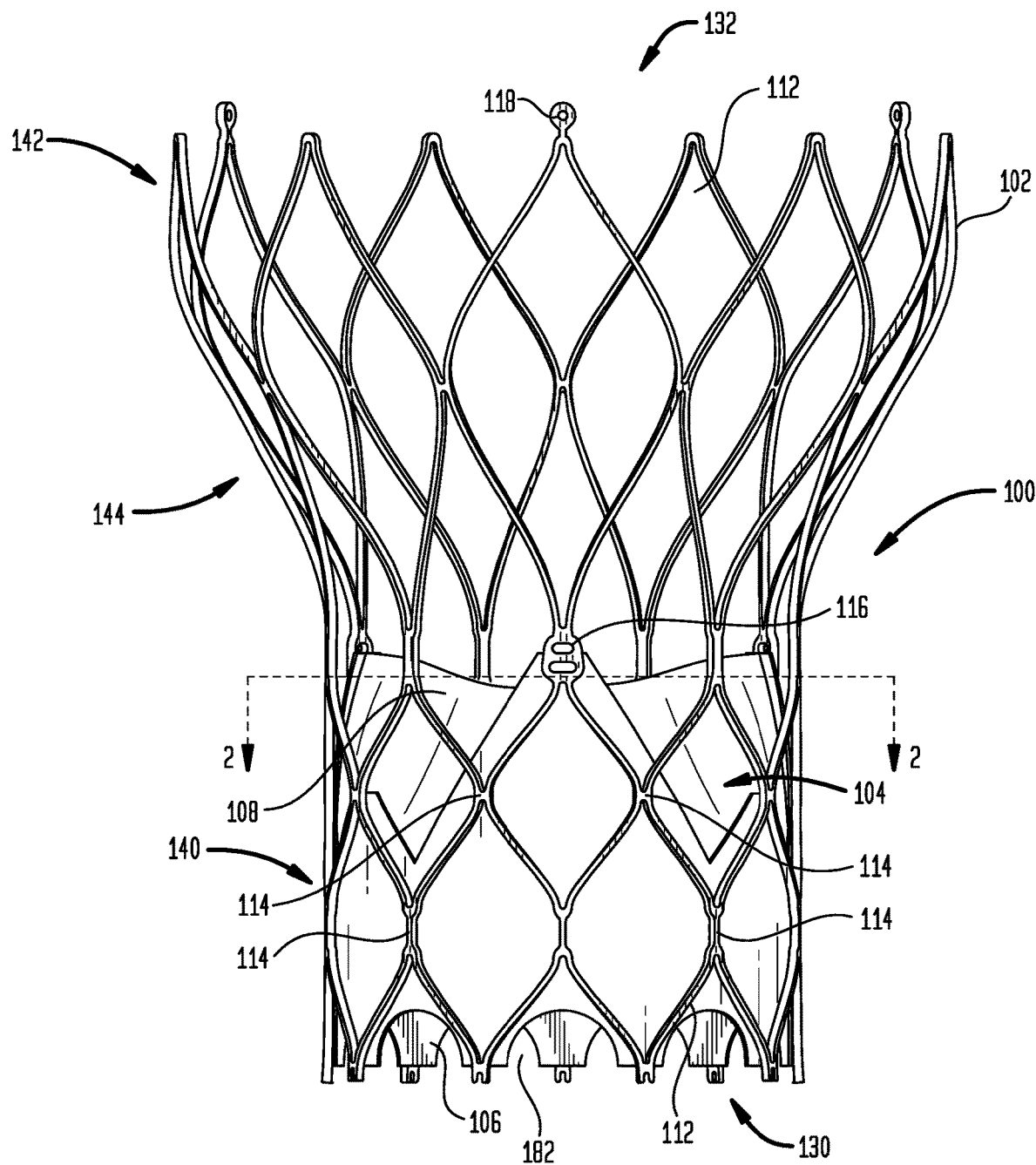
FIG. 1 is a front view of a conventional collapsible prosthetic heart valve.

FIG. 1 shows a collapsible stent-supported prosthetic heart valve 100 known in the art. The prosthetic heart valve 100 is designed to replace the function of a native tricuspid, bicuspid or unicuspid valve of a patient, such as a native aortic valve. It should be noted that while the embodiments herein are described predominately in connection with their use with a prosthetic aortic valve and a stent having a shape as illustrated in FIG. 1, the embodiments may also be used with tricuspid valves, pulmonic valves, and bicuspid valves, such as the mitral valve, and with stents having different shapes, such as those having a flared or conical annulus section, a less-bulbous aortic section, and the like, and a differently shaped transition section.

The prosthetic heart valve 100 includes a stent constructed as a frame 102 from a plurality of attached cells 112, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including shape memory alloys known as Nitinol. Suitable synthetic polymers for use as a stent include, but are not limited to, thermoplastics, such as polyolefins, polyesters, polyamides, polysulfones, acrylics, polyacrylonitriles, polyetheretherketone, and polyaramides.

The stent 102 extends from a proximal or annulus end 130 to a distal or aortic end 132, and includes an annulus section 104 adjacent the proximal end 130 and an aortic section 142 adjacent the distal end 132. The annulus section 104 has a relatively small cross-section in the expanded condition, while the aortic section 142 has a relatively large cross-section in the expanded condition. The annulus section 104 may be in the form of a cylinder having a substantially constant diameter along its length. A transition section 144 may taper outwardly from the annulus section 104 to the aortic section 142. Each of the sections of the stent 102 includes a plurality of cells 112 connected to one another in one or more annular rows around the stent 102. For example, as shown in FIG. 1, the annulus section 104 may have two annular rows of complete cells 112 and the aortic section 142 and the transition section 144 may each have one or more annular rows of complete or partial cells 112. The cells 112 in the aortic section 142 may be larger than the cells 112 in the annulus section 104. The larger cells 112 in the aortic section 142 better enable the prosthetic valve 100 to be positioned without the stent structure 102 interfering with blood flow to the coronary arteries. The cells 112 may be connected circumferentially to each other by runners 114 arranged about the stent 102.

The stent 102 may include one or more retaining elements 118 at the distal end 132 thereof, the retaining elements 118 being sized and shaped to cooperate with retaining structures provided on a deployment device (not shown). The engagement of the retaining elements 118 with the retaining structures on the deployment device helps maintain the prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and during deployment.

The stent 102 may also include a plurality of commissure points 116 for mounting the commissures (not identified), where two leaflets 108 come together to the stent 102. As can be seen in FIG. 1, the commissure points 116 may lay at the intersection of four cells 112, two of the cells 112 being adjacent one another in the same annular row, and the other two cells 112 being in different annular rows and lying in end-to-end relationship. In one embodiment, the commissure points 116 are positioned entirely within the annulus section 104 or at the juncture of annulus section 104 and the transition section 144. The commissure points 116 may include one or more eyelets which facilitate the suturing of the leaflet commissure to the stent.

The prosthetic heart valve 100 includes a valve assembly 140 preferably positioned in the annulus section 104. The valve assembly 140 may be mounted to the stent 102 by suturing the commissures of the leaflets 108 to the commissure points 116 and suturing other portions of the valve assembly 140 to the stent 102, or by other methods known in the art. The valve assembly 140 may include a cuff 106 and a plurality of leaflets 108 which collectively function as a one-way valve by coapting with one another. FIG. 1 illustrates a prosthetic heart valve for replacing a native tricuspid valve, such as the aortic valve. Accordingly, the prosthetic heart valve 100 is shown in FIG. 1 with three leaflets 108, as well as three commissure points 116. However, it will be appreciated that the prosthetic heart valves according to aspects of the disclosure may have a greater or lesser number of leaflets 108 and commissure points 116. The valve assembly 140 may be wholly or partly formed of any suitable biological material or polymer. Examples of biological materials suitable for the valve assembly 140 include, but are not limited to, porcine or bovine pericardial tissue. Examples of polymers suitable for the valve assembly 140 include, but are not limited to, polyurethane, silicone, PTFE and polyester. In at least some examples, portions of valve assembly 140, the cuff and the suture used may include an ultra-high molecular weight polyethylene.

Although the cuff 106 is shown in FIG. 1 as being disposed on the luminal or inner surface of the annulus section 104, it is contemplated that the cuff 106 may be disposed on the abluminal or outer surface of annulus section 104, or may cover all or part of either or both of the luminal and abluminal surfaces of the annulus section 104. Both the cuff 106 and the leaflets 108 may be wholly or partly formed of any suitable biological material or polymer, including those, such as PTFE, described above in connection with the prosthetic heart valve 100. Additionally, the cuff 106 may be formed from polyurethane copolymers or include ultra-high molecular weight polyethylene.

As is shown in FIG. 1, in one example the entirety of the valve assembly 140, including the leaflet commissures, is positioned in the annulus section 104 of the stent 102. When opened, the leaflets may extend further into the transition region 144 or may be designed such that they remain substantially completely within the annulus region 104. In this embodiment, substantially the entirety of the valve assembly 140 is positioned between the proximal end 130 of stent 102 and the commissure points 116, and none of the valve assembly is positioned between the commissure points 116 and the distal end 132 of the stent 102.

In operation, the embodiments of the prosthetic heart valve 100 described above may be used to replace a native heart valve, such as the aortic valve, a surgical heart valve or a heart valve that has undergone a surgical procedure. The prosthetic heart valve 100 may be delivered to the desired site (e.g., near a native aortic annulus) using any suitable delivery device. During delivery, the prosthetic heart valve 100 is disposed inside the delivery device in the collapsed condition. The delivery device may be introduced into a patient using any known procedures, such as a transfemoral, transapical or transseptal approach. Once the delivery device has reached the target site, the user may deploy the prosthetic heart valve 100. Upon deployment, the prosthetic heart valve 100 expands into secure engagement within the native aortic annulus. When the prosthetic heart valve 100 is properly positioned inside the heart, it works as a one-way valve, allowing blood to flow in one direction and preventing blood from flowing in the opposite direction.

Figure 2:
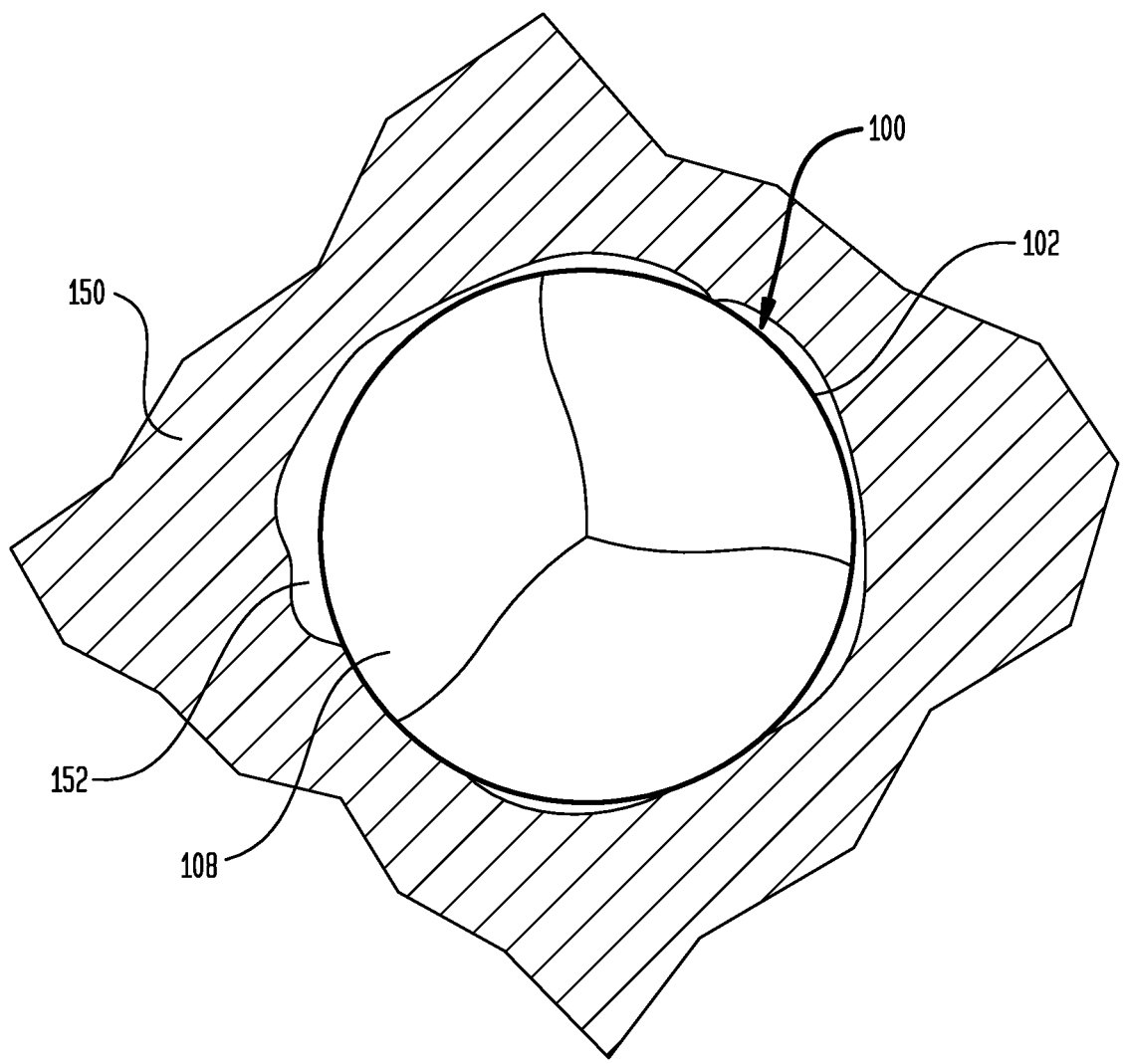
FIG. 2 is a top cross-sectional view of the prosthetic heart valve of FIG. 1 implanted in a patient taken along Line 2-2 in FIG. 1.

FIG. 2 is a cross-sectional illustration of the prosthetic heart valve 100 having leaflets 108 disposed within the native valve annulus 150, taken along line 2-2 shown in FIG. 1. As seen in FIG. 2, the substantially circular annulus section of the stent 102 is disposed within a non-circular native valve annulus 150. At certain locations around the perimeter of the prosthetic heart valve 100, gaps 152 form between the heart valve 100 and the native valve annulus. Blood flowing through these gaps and around the valve assembly 140 of the prosthetic heart valve 100 can result in paravalvular leak or regurgitation and other inefficiencies which can reduce cardiac performance. Such improper fitment may be due to suboptimal native valve annulus geometry due, for example, to calcification of the native valve annulus or due to unresected native leaflets.

In accordance with the various embodiments of the present disclosure, stent assemblies for use in a prosthetic heart valve incorporating multiple design concepts of a cuff feature for eliminating paravalvular leakage will be described. As to be described hereinafter in greater detail, one or more members may be coupled to a portion of the stent's cuff and to additional stent features such as the runners 114 to position the cuff about the abluminal surface of the stent upon deployment from a delivery device to seal in and around any calcific nodules. Prosthetic heart valves having such a cuff pursuant to the embodiments of the present disclosure decrease delivery system volume and profile of the prosthetic heart valve. The cuff sealing material being coupled to the members is positioned out of the area of most volume providing a low profile prosthetic heart valve. When deployed, the members, such as formed from shape memory materials, relax from their tensioned state and position the cuff sealing material in the sealing region of the prosthetic heart valve to reduce paravalvular leakage. Various embodiments of a prosthetic heart valve including a stent assembly having such a cuff pursuant to the present disclosure will now be described.

Figure 3:
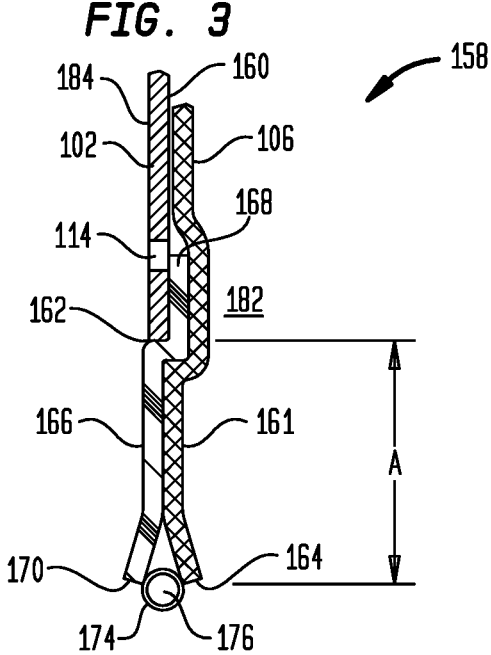
FIG. 3 is a cross sectional view of a prosthetic heart valve including a stent assembly having a cuff in accordance with one embodiment of the disclosure shown coupled to members in a tensioned state.
Figure 4:
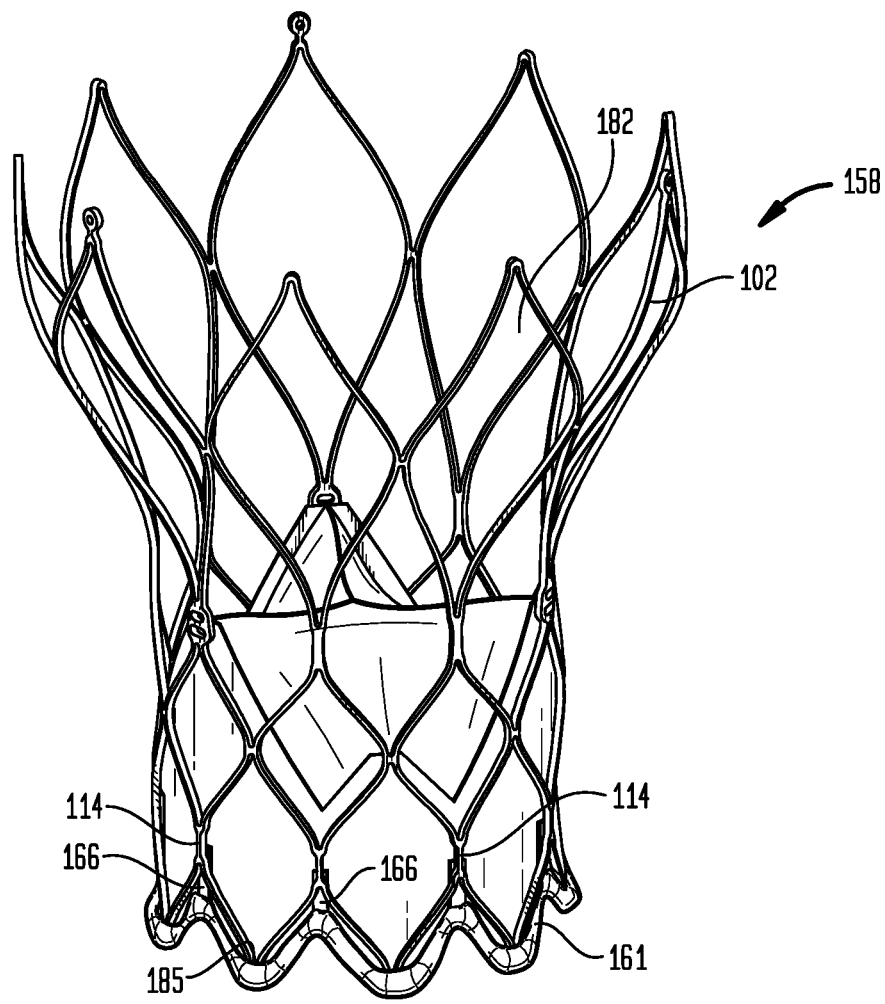
FIG. 4 is a perspective view of the prosthetic heart valve of FIG. 3 showing the members in a relaxed state forming a cuff seal.

Referring to FIGS. 3 and 4, a prosthetic heart valve 158 is shown which includes a stent 102 provided with a cuff 106 at least partially disposed over its luminal surface 160 such as shown in FIG. 1 thereby forming a stent assembly. The cuff 106 has an extended cuff portion 161 which extends outwardly beyond the proximal end 162 of the stent coupled to at least one member 166 shown under tension. In the embodiment being described, the distance between the proximal end 162 of the stent 102 and the proximal end 164 of the extended cuff portion 161 may be in one example about 2 mm as designated by dimension A. As will be understood from the various embodiments of the disclosure to be described, dimension A can be varied depending upon the desired position of the extended cuff portion 161 when positioned by the members 166. The cuff 106 and extended cuff portion 161 may be one integral unitary member, or two or more members sutured together. In either case, they may be formed from a variety of materials as previously described with respect to cuff 106, including, but not limited to bovine/porcine tissue (glycerol impregnated or freeze dried), radiopaque fabric/tissue, braided or weaved fabric (PTFE, PET, UHMWPE), PTFE or gel/collagen coated fabric, multi-layered composite/sheets of any of these materials (e.g., fabric/tissue composites), etc.

The extended cuff portion 161 may be coupled to the stent 102 by a plurality of circumferentially arranged elongated members 166 positioned around the stent, and in particular, between the cuff and the stent to reduce stent volume or bulk. The distal end 168 of the members 166 may be attached to the runners 114 of the stent 102 between the cuff 106 and the stent frame using known suturing techniques. The proximal end 170 of the members 166 and the proximal end 164 of the extended cuff portion 161 may be coupled to a ring shaped hollow tube 174 which defines a lumen 176. The hollow tube 174 can be constructed as a fabric tube from the same or different materials as the cuff 106 described above. The members 166 may be sutured to the hollow tube 174 using known suturing techniques, by way of example, using a single knotted stitch, followed by a double knot as known in the surgical field. On the other hand, the extended cuff portion 161 may be coupled to the hollow tube 174 using a running whip stitch as known in the surgical field.

The members 166, in accordance with the present disclosure, have dimensional and/or shape memory properties, which after being tensioned, will return to their original dimensions and/or shape after the tensioning force is removed, i.e., relaxed state. Suitable materials for the members 166 may comprise, by way of example, synthetic polymer material such as polypropylene and elastic silicones; natural rubber, super-elastic material, and elastic metals; and shape memory material and shape memory alloys such as Nitinol. The members 166 may be in accordance with one embodiment in the nature of an elongated rectangular strip such as an elastic band wherein the members may be placed under tension by elongating from their relaxed or original state. In other embodiments, the members 166 may be configured as elements which return to their original dimension and/or shape after a tension force is removed such as springs, e.g., coiled springs and the like. Upon release of the tension, the members will revert to their original length dimension and/or shape. In the embodiment described thus far with respect to FIGS. 3 and 4, the members 166 may be in the nature of bands of elastic material about 3 mm in width and about 4 mm in length when relaxed. In accordance with other embodiments, the members 166 may be in the nature of coiled springs of biocompatible material or shape memory material such as Nitinol. Accordingly, the members may have different forms and different material properties and characteristics to allowing tensioning and return to their original dimensions and/or shape after the tension force is removed.

In the embodiment shown in FIGS. 3 and 4, the distal end 168 of the members 166 are attached to the nine runners 114 provided circumferentially about the stent 102 adjacent the stent's proximal end using any suitable technique, such as suturing and the like. However, the members 166 may also be attached to the stent's joints, struts or any other valve or stent feature. As best shown in FIG. 4, the runners 114 are located between adjacent cells forming the first proximal row of the stent frame 102. In the event of a greater number of cells and runners, it is contemplated that there will be a corresponding increase in the number of members 166 used for coupling the extended cuff portion 161 to the stent, although not a requirement of the disclosure. It is therefore not required that a member 166 be attached to each of the runners 114 or other attachment features on the stent 102. In particular, the number of members 166 may be less than the number of runners or other such features to which the members could be attached. In addition, it is not required that the members 160 be attached symmetrical about the stent 102, rather, the members can be attached asymmetrical about the stent and at different distances between the distal and proximal ends of the stent.

The members 166 as shown in FIG. 3 have been tensioned thereby positioning a portion of the extended cuff portion 161 outwardly of the proximal end 162 of the stent 102. This initial configuration produces a low profile stent as the extended cuff portion 161 (which will form the cuff seal) and members 166 are generally positioned within the lumen 182 formed by the stent frame as opposed to being supported externally on the abluminal surface 184 of the stent. The extended cuff portion 161 and members 166 can be pulled-up, twisted-up, folded-up, rotated-up, inverted-up and the like into the lumen 182 prior to positioning the stent 102 in the catheter of the delivery device. When being deployed from the delivery device, the members 166 will transform the shape of the extended cuff portion 166 from one of its aforementioned shapes into the final shape of the cuff seal as shown in the various embodiments of the disclosure. By way of one example, by pulling on and inverting the extended cuff portion from its delivery configuration or shape to its deployed configuration or shape thereby forming the cuff seal.

In the orientation disclosed in FIG. 3, the low profile stent 102 can be inserted, typically after being collapsed, into the lumen of a catheter delivery device for delivery to a native aortic valve using known surgical procedures and delivery devices. Upon removal from the delivery device, the members 166 will relax to their original non-tensioned state. As a result, the members 166 will pull the extended cuff portion 161 and the hollow tube 174 out of the lumen 182 and then over the stent's proximal edge towards the distal end of the stent. At least a portion of the extended cuff portion 161 and hollow tube 174 will now be disposed over the lower abluminal surface 184 of the stent adjacent the stent's proximal edge. By attaching the members 166 to the runners 114 adjacent the proximal end of the stent 102, the extended cuff portion 161 and hollow tube 174 are pulled upwardly over the proximal edge of the stent into an undulating cuff seal 185. The undulating pattern is provided by the bottom row of cells 112 forming the stent 102 which are open facing proximally as shown in FIG. 1. Accordingly, the extended cuff portion 161 and hollow tube 174 conform to the shape of the bottom most rows of cells 112 in the stent 102. The extended cuff portion 161 extends outwardly of the abluminal surface 184 of the stent for engagement with patient's tissue to form a seal thereat, thereby preventing paravalvular leakage.

Figure 5:
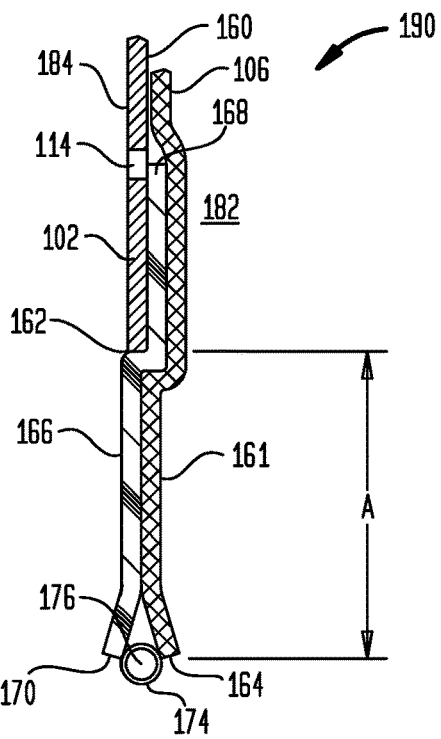
FIG. 5 is a cross sectional view of a prosthetic heart valve including a stent assembly having a cuff in accordance with another embodiment of the disclosure coupled to members in a tensioned state.
Figure 6:
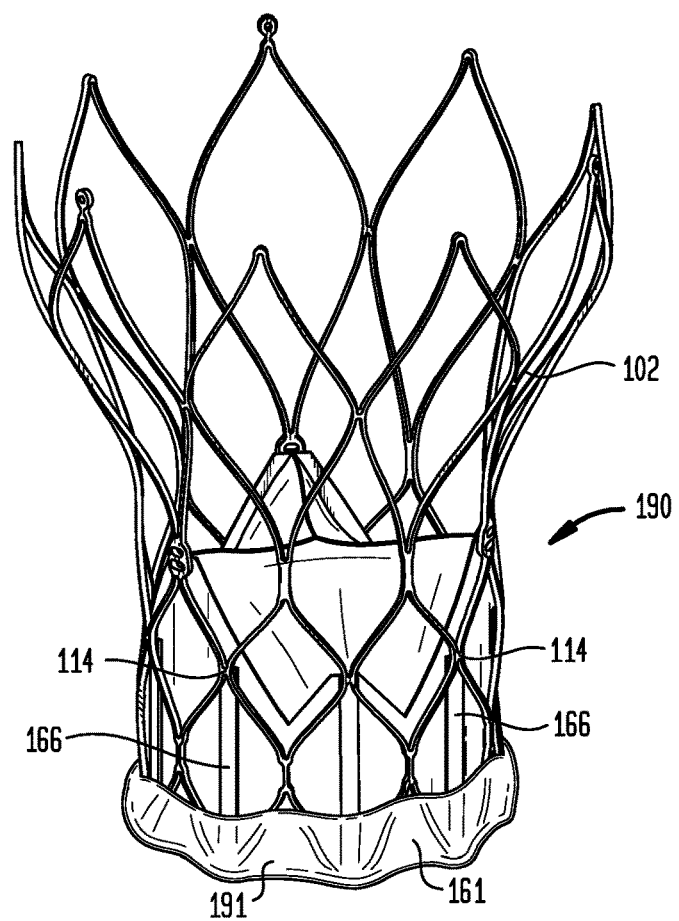
FIG. 6 is a perspective view of the prosthetic heart valve of FIG. 5 showing the members in a relaxed state forming a cuff seal.

Referring to FIGS. 5 and 6, another embodiment of a prosthetic heart valve 190 including a stent 102 having a cuff forming a stent assembly is disclosed. The prosthetic heart valve 190 is of similar construction to the prosthetic heart valve 158 disclosed in FIG. 3. In the prosthetic heart valve 190 of FIG. 5, the distal end 168 of the members 166 are attached to the runners 114 at the mid-peak or mid-joint of the stent 102. In addition, the extended cuff portion 161 extends a greater distance beyond the proximal end 162 of the stent 102 then in the prosthetic heart valve 158 of FIG. 3. In accordance with this embodiment, the dimension A may be approximately 6 mm, i.e., the distance between the proximal end 162 of the stent 102 and the proximal end 164 of the extended cuff portion 161. It is contemplated that at the members 166 will therefore be larger than those described in FIG. 3, for example, about 5 mm wide and about 8 mm long.

In FIG. 5, the members 166 are shown under tension by being elongated thereby displacing the proximal end 164 of the extended cuff portion 161 outwardly from the proximal end 162 of the stent 102. The members 166 and extended cuff portion 161 are now configured to be generally confined within the lumen 182 of the stent upon insertion into a catheter of a delivery device. At the location of delivery of the prosthetic heart valve 190, the members 166 relax thereby pulling the extended cuff portion 161 and hollow tube 174 out of the lumen 182 and then in a direction towards the distal end of the stent. As a result, a portion of the extended cuff portion 161 is arranged overlying and circumscribing the abluminal surface 184 of the stent as shown in FIG. 6. As the members 166 are attached to runners 114 at the mid-peak or mid-joint of the stent, i.e., distally displaced further away from the runners as shown in the embodiment of FIG. 3, the extended cuff portion 161 and hollow tube 174 form a gathered ring of cuff sealing material 191 circumscribing adjacent the proximal end 162 of the stent 102, generally lacking the previous undulating pattern.

Figure 7A:
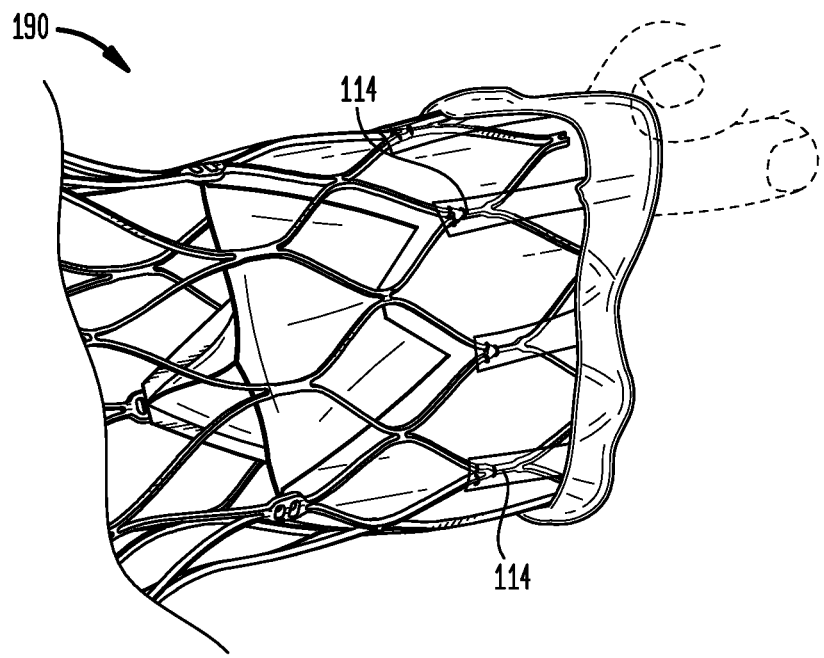
FIGS. 7A and 7B are perspective views of the prosthetic heart valve of FIG. 6 being prepared for insertion into the lumen of a catheter delivery system by placing the members under tension.
Figure 7B:
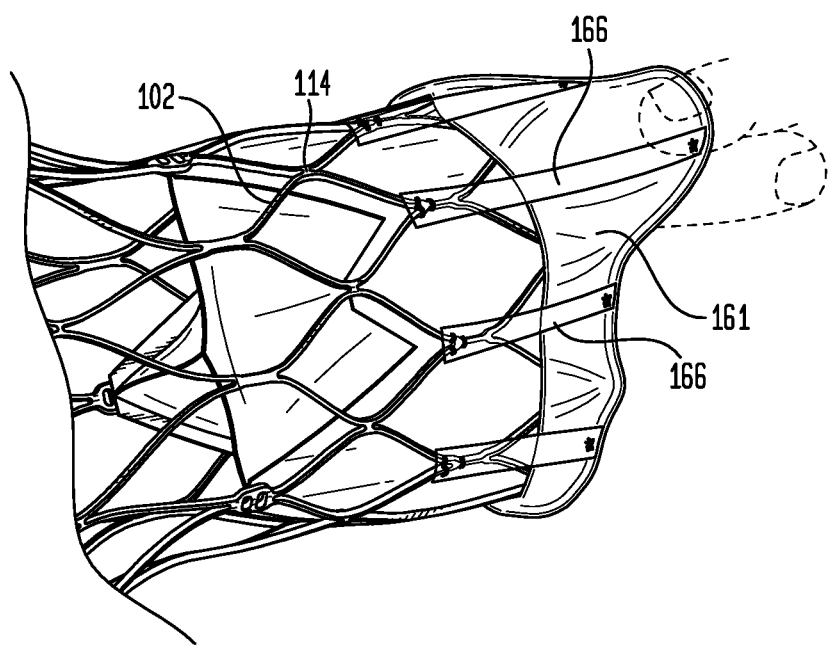
Figure 8:
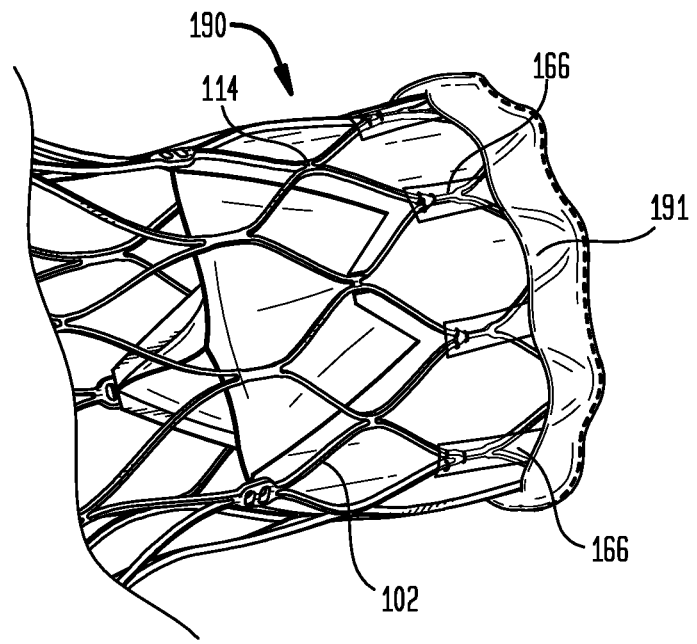
FIG. 8 is a perspective view of the prosthetic heart valve shown in FIG. 7 after being deployed from the delivery system.

Referring to FIGS. 7A and 7B, the prosthetic heart valve 190 is shown being prepared to be received within a catheter of a delivery device. The extended cuff portion 161 is pulled against the resistance of the members 166 from their relaxed orientation (FIG. 7A) in an outwardly proximal direction around the stent to place the members 166 under tension, as shown in FIG. 7B. The extended cuff portion 161 is then finally positioned within the lumen 182 to reduce bulk volume during sheathing of the stent. In FIG. 8, the prosthetic heart valve 190 is shown after deployment from the delivery device where the members 166 have relaxed with the extended cuff portion 161 and hollow tube 174 arranged circumscribing the proximal end of the stent 102 overlying the abluminal surface 184 forming the cuff seal 191.

Figure 9:
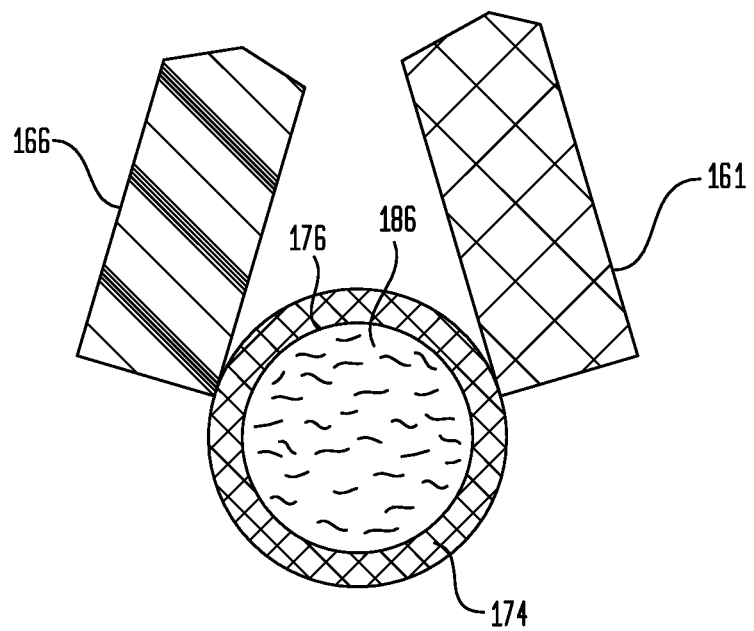
FIG. 9 is a cross sectional view of the fiber hollow tube of the prosthetic heart valve of FIGS. 3 and 5 including an insert in the nature of filler material.

To enhance the sealing effect of the cuff to prevent paravalvular leakage, the hollow tube 174 may contain an insert such as filler material or an elongated coiled member. By way of example, as shown in FIG. 9, the lumen 176 of the hollow tube 174 has been filled with expandable material. By way of example, expandable material may include PVA, polyacrilimide, shape memory foam, collagen, and the like to increase sealing bulk. Further, the filler material may include a highly compressible sponge made from alginate cross linked at low temperature. This type of gel will collapse to a large extent when shear forces are applied and return to its original shape when the forces are removed. As a result of the compressibility of this type of material, it will contribute to a low prosthetic heart valve profile, and will spring back when deployed to provide an effective paravalvular leak seal. It is further contemplated that other biocompatible materials can be used for the filler material in accordance with other embodiments of the present disclosure.

Figure 10:
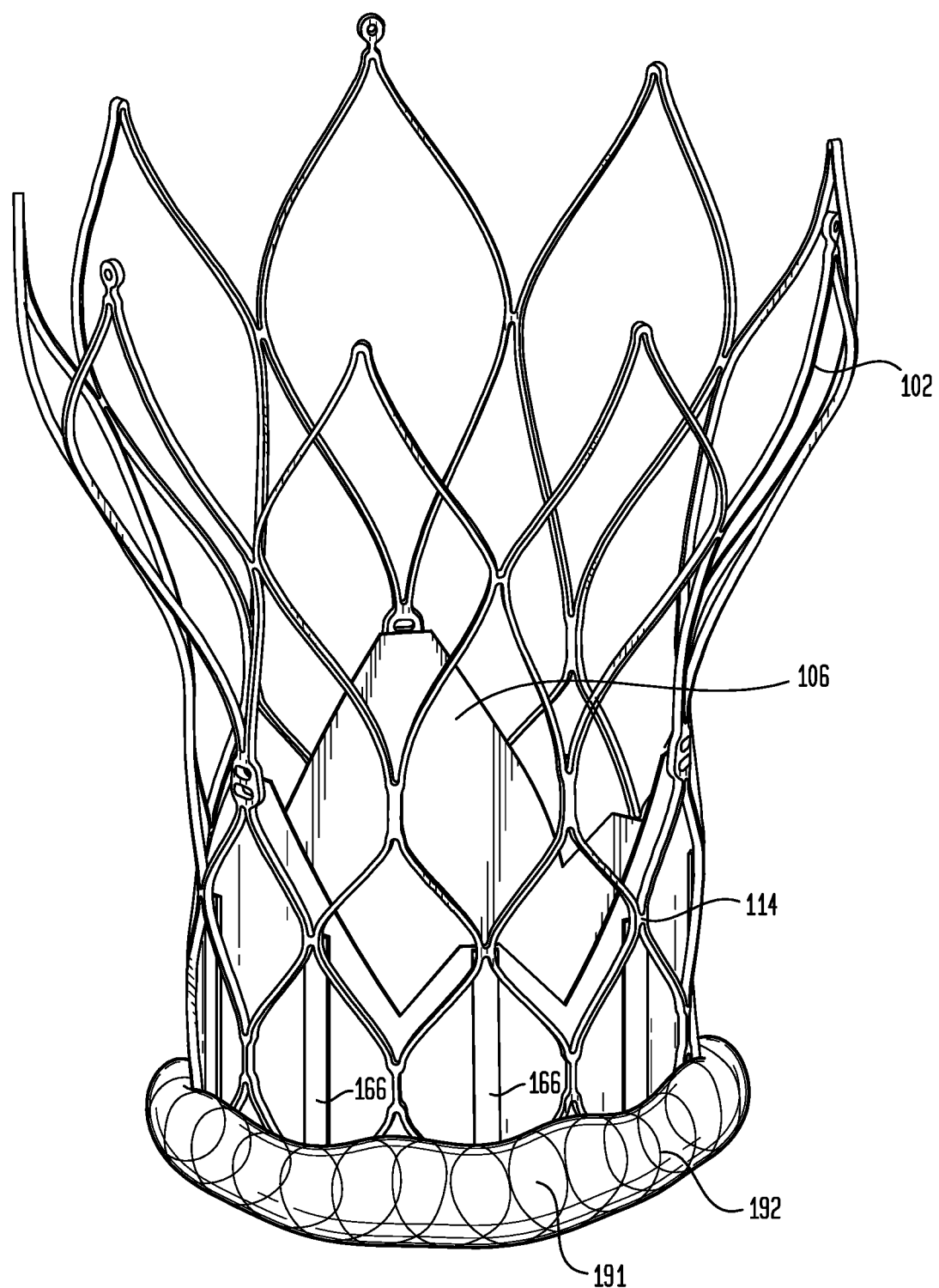
FIG. 10 is a perspective view of the prosthetic heart valve showing the fiber hollow tube of FIGS. 3 and 5 having an insert in the nature of a coiled member.

As shown in FIG. 10, the insert may include an elongated coil member 192 or other shaped members formed from various materials such as biocompatible polymers and metals and metal alloys. For example, the coil member 192 may be formed of materials similarly used for the construction of the stent 102 such as Nitinol which can be collapsed and then returned to its original shape after deployment of the stent.

Figure 11:
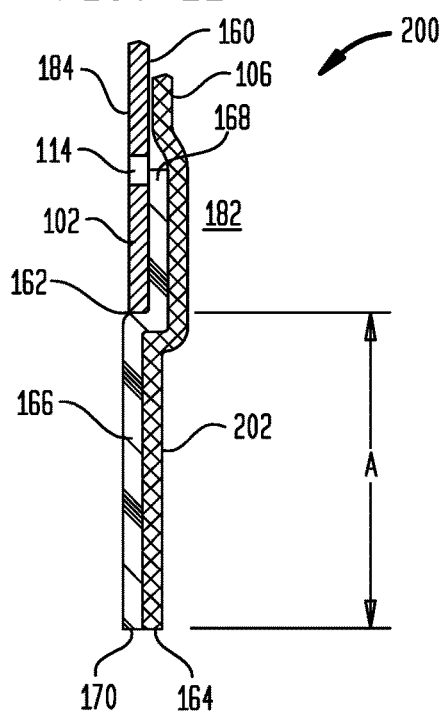
FIG. 11 is a cross sectional view of a prosthetic heart valve including a stent assembly having a cuff in accordance with another embodiment of the disclosure coupled to members in a tensioned state.
Figure 12:
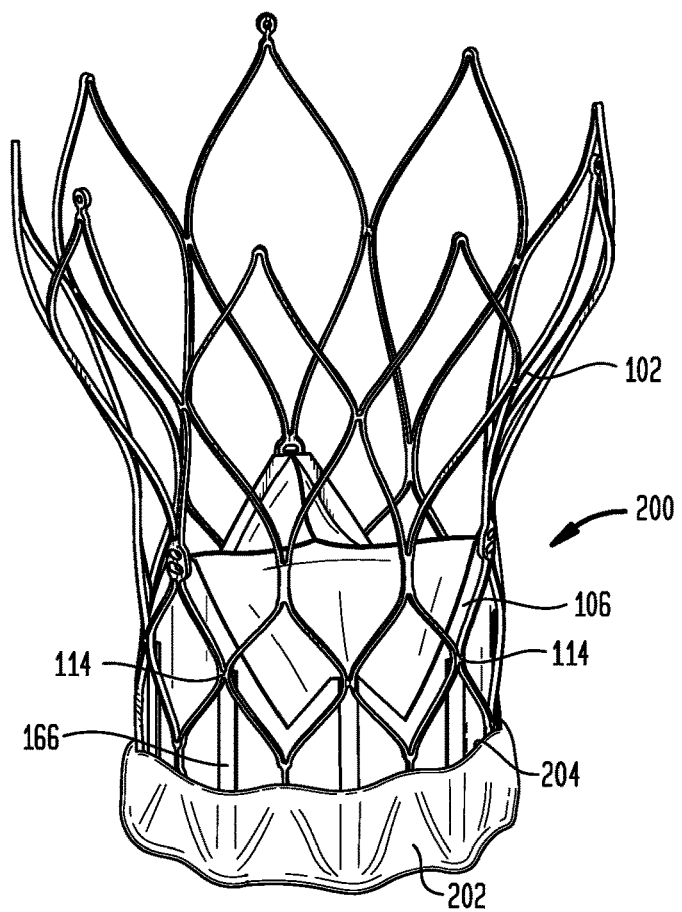
FIG. 12 is a perspective view of the prosthetic heart valve of FIG. 11 showing the members in a relaxed state forming a cuff seal.

Referring now to FIGS. 11 and 12, another embodiment of a prosthetic heart valve 200 having a stent assembly will be described. As shown in FIG. 11, as in the previous embodiments, the prosthetic heart valve 200 includes a cuff 106 coupled to the stent 102 disposed over the luminal surface 160 and a plurality of members 166 shown under tension thereby forming a stent assembly. The distal ends 168 of the members 166 are coupled between the cuff 106 and stent 102 to the runners 114 at the stent's mid-joint or mid-peak, circumferentially around the stent using known suturing techniques. The cuff 106 is provided with an extended cuff portion 202 projecting outwardly from the proximal end 162 of the stent 102. By way of one example, the extended cuff portion 202 may have a length of approximately 9 mm below the proximal end 162 of the stent. In this embodiment, the members 166 formed of elastic material may have a width of about 5 mm. and a length of about 8 mm. The proximal end 170 of the members 166 is sutured to the proximal end 164 of the extended cuff portion 202 by suitable suturing techniques, such as using a single/double knot on the abluminal side as is known in the surgical field.

As shown in FIG. 12, when the members 166 are relaxed from their tensioned state as shown in FIG. 11, the members recoil and pull the extended cuff portion 202 out of the lumen 182 and then in a direction towards the distal end of the stent 102 over a portion of the abluminal surface 184 of the stent. This forms a continuous expandable pocket 204 between the extended cuff portion 202 and abluminal surface 184 of the stent 102 about the annulus section 104. The pocket 204 is open facing in a distal direction circumscribing the stent 102, while closed facing in a proximal direction. The height of the pocket can be modified by changing the length of the extendable cuff portion 202. The pocket 204 receives fluid pressure in the patient's artery when deployed as an aortic valve to expand and seal around calcified nodules.

Figure 13:
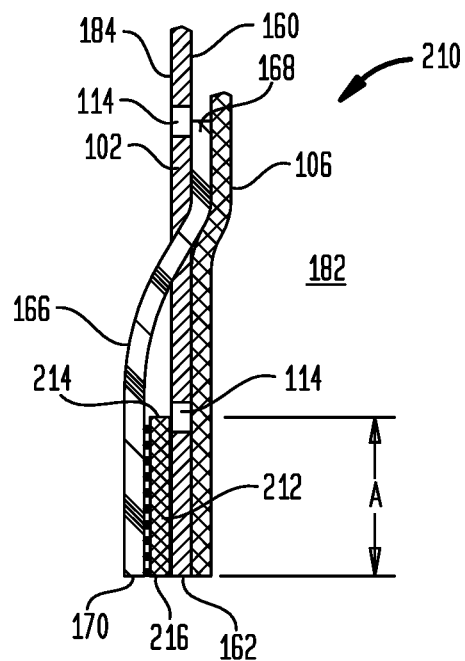
FIG. 13 is a cross sectional view of a prosthetic heart valve including a stent assembly having a cuff in accordance with another embodiment of the disclosure coupled to members in a tensioned state.
Figure 14:
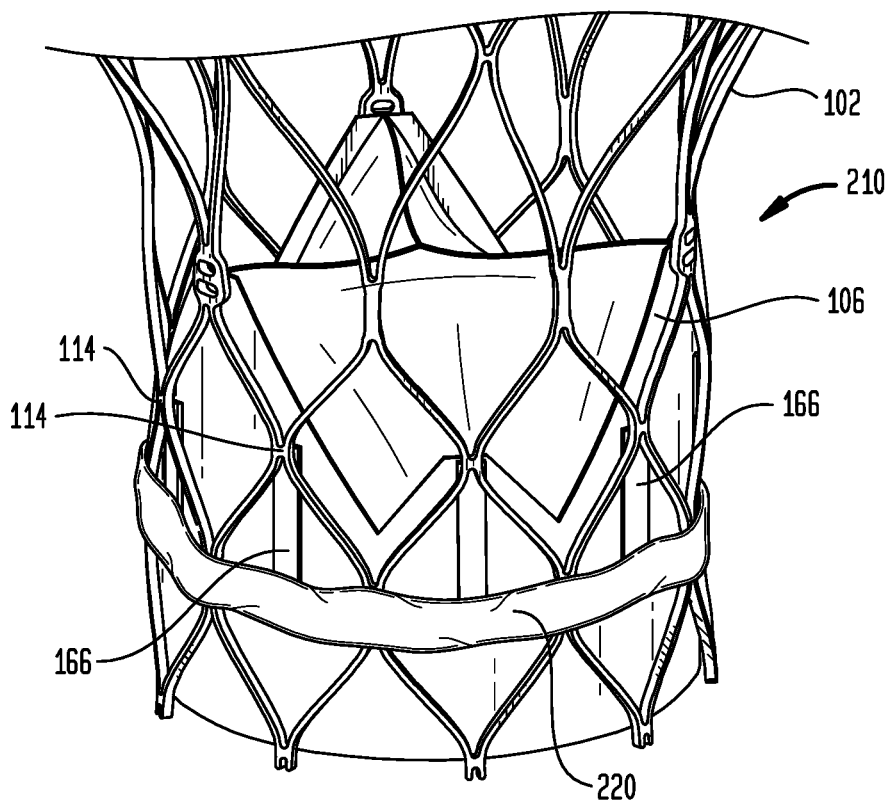
FIG. 14 is a perspective view of the prosthetic heart valve of FIG. 13 showing the members in a relaxed state forming a cuff seal.

Referring now to FIGS. 13-14, there will be described a prosthetic heart valve 210 having a stent assembly in accordance with another embodiment of the present disclosure. As shown in FIG. 13, the members 166 under tension have their distal ends 168 coupled to the runners 114 at the mid-joint or mid-peak of the stent 102 between the cuff 106 and the stent using suitable suturing techniques thereby reducing the bulk or volume of the stent. The members 166 extend outwardly overlying the abluminal surface 184 of the stent 102 in a proximal direction. The proximal ends 170 of the members 166 are generally arranged adjacent the proximal end 162 of the stent 102.

As previously described, the members 166 may be constructive in the nature of elongated bands of elastic material. In the embodiment of FIG. 13, the members 166 may be approximately 5 mm in width and 8 mm in length. A panel 212 of sealing material is arranged overlying the abluminal surface 184 of the stent 102 adjacent the proximal end 162 of the stent. The sealing material 212 may be in the nature of a rectangular elongated panel circumscribing the stent 102. The sealing material 212 can be provided from material similar to cuff 106 so as to form a seal to prevent paravalvular leakage when the prosthetic heart valve 210 is positioned in a native aortic valve. In this embodiment the panel 212 may have a height of about 9 mm.

The distal end 214 of the panel of sealing material 212 is coupled to runners 114 about the circumference of the stent 102 using any suitable suturing technique as known in the art. The proximal end 216 of the panel of sealing material 212 terminates adjacent the proximal end 162 of the stent 102 and is not attached thereto. Rather, the proximal end 170 of the members 166 is coupled on the abluminal side to the proximal end 216 of the panel of sealing material 212 using a single/double knot as is known in the surgical field. In addition, each of the members 166 are coupled to the panel of sealing material 212 using an alternating running stitch from the distal end 214 to the proximal end 216 of the sealing material along longitudinal axes of the stent 102 while the members are under tension by being elongated.

Referring to FIG. 14, when the members 166 are relaxed, the relaxed state causes the panel of sealing material 212 to fold back upon itself in a direction towards the distal end of the stent over the abluminal surface 184 of the stent 102 to create a bunched-up ring of sealing material 220 at the location of the runner 114 to which the distal end 214 of the sealing material was attached. The location of the sealing material can be changed by altering the runner attachment location along the stent in the proximal/distal direction.

Although certain embodiments of the prosthetic heart valve having a stent assembly as described herein may provide a single feature for reducing paravalvular leakage, it should be understood that multiple similar or dissimilar features may be utilized on a single prosthetic heart valve to reduce paravalvular leakage. Various embodiments of a low profile prosthetic heart valve have been described in accordance with the present disclosure. In certain embodiments, an extended cuff is coupled to the stent with a plurality of members in the nature of elongated shape memory material such as elastic members or shape memory members, or coiled members to provide a low profile prosthetic heart valve for catheter delivery. The members are initially placed under tension to maintain an extended cuff portion in a first orientation such as outwardly of the proximal end of the stent. Upon relaxing the tension in the members, the extended cuff portion is pulled towards the distal end of the stent over the abluminal surface to form a cuff seal at various locations along the stent in the annulus section. In some embodiments, the cuff seal is in the nature of a circumscribing expandable pocket, the height of which can be modified. Prosthetic heart valves with expandable pockets are described in greater detail in U.S. Patent Publication No. 2011/0098802, the disclosure of which is hereby incorporated by reference herein. In other embodiments of the present disclosure, a panel of sealing material may be placed circumferentially about the abluminal surface of the stent to which the members are coupled. In the various embodiments, the members remain coupled to the cuff material and stent as an integral component of the prosthetic heart valve when replacing native valves.

A prosthetic heart valve incorporating a stent assembly for replacing a native valve in accordance with one embodiment of the disclosure is constructed from a stent having a luminal surface and an abluminal surface extending between a distal end and a proximal end thereof; a valve may be disposed within the stent; a cuff coupled to the stent having a first orientation and a second orientation; and a plurality of members having a distal end coupled to the stent and a proximal end coupled to the cuff, the plurality of members having a first state when the cuff is arranged in the first orientation and a second state when the cuff is arranged in the second orientation.

In the aforesaid prosthetic heart valve, wherein the plurality of members have a distal end and a proximal end, and wherein the proximal end of the plurality of members are coupled to the cuff at spaced apart circumferential locations around the stent; and/or wherein the stent includes a plurality of runners, and wherein the distal end of the plurality of members are coupled to the runners; and/or wherein the cuff includes a distal end and a proximal end, and wherein the plurality of members include a distal end and a proximal end, and further including a hollow tube coupled to the proximal ends of the cuff and the plurality of members; and/or wherein the hollow tube defines a lumen, and further including an insert disposed within the lumen; and/or wherein the insert comprises at least one of a filler material or an elongated coiled member; and/or wherein the plurality of members are attached to the cuff circumferentially along spaced apart longitudinally extending axes of the stent; and/or wherein at least a portion of the cuff is at least partially positioned outward of the proximal end of the stent when arranged in the first orientation and at least partially disposed on the abluminal surface of the stent when arranged in the second orientation; and/or wherein the members comprise elastic members having a tensioned first state and a relaxed second state.

A prosthetic heart valve incorporating a stent assembly for replacing a native valve in accordance with one embodiment of the disclosure is constructed from a stent having a proximal end and an abluminal surface; a valve may be disposed within the stent; and a cuff coupled to the stent by a plurality of members having a relaxed state and a tensioned state for orienting at least a portion of the cuff at least partially disposed on the abluminal surface when the plurality of members are in a relaxed state.

In the aforesaid prosthetic heart valve, wherein at least a portion of the cuff is arranged at least partially outward of the proximal end of the stent when the plurality of members are in a tensioned state; and/or wherein the stent includes a plurality of runners, and wherein the plurality of members have a distal end and a proximal end, the distal end of the plurality of members is coupled to one of the runners and the proximal end of the plurality of members is coupled to a portion of the cuff; and/or wherein the cuff is at least partially disposed on the abluminal surface of the stent when the plurality of members is in the tensioned state and relaxed state; and/or wherein the plurality of members are attached to the cuff circumferentially along spaced apart longitudinally extending axes of the stent; and/or wherein the cuff includes a distal end and a proximal end, and wherein the plurality of members include a distal end and a proximal end, and further including a hollow tube coupled to the proximal ends of the cuff and the plurality of members, and an insert comprising at least one of a filler material or an elongated coiled member disposed within the hollow tube; and/or wherein the plurality of members comprise elastic members.

A prosthetic heart valve incorporating a stent assembly for replacing a native valve in accordance with one embodiment of the disclosure is constructed from a stent configured to have a collapsed condition and an expanded condition, the stent having a luminal surface and an abluminal surface extending between a distal end and a proximal end thereof; and a valve assembly may be disposed within the stent, the valve assembly including a plurality of leaflets and a cuff having a portion at least partially disposed on the luminal surface of the stent; at least a portion of the cuff having a first orientation extending outwardly of the proximal end of the stent or at least partially disposed on the abluminal surface of the stent, and a second orientation with a portion of the cuff at least partially disposed on the abluminal surface of the stent; and a plurality of elongated elastic members having a distal end coupled to the stent and a proximal end coupled to the cuff at circumferentially spaced apart locations, the plurality of elastic members having a tensioned state when the cuff is arranged in the first orientation and a relaxed state when the cuff is arranged in the second orientation.

In the aforesaid prosthetic heart valve, wherein the stent includes a plurality of runners, and wherein the distal end of the plurality of elastic members are coupled to the runners; and/or wherein the cuff includes a distal end and a proximal end, and wherein the plurality of elastic members include a distal end and a proximal end, and further including a hollow tube coupled to the proximal ends of the cuff and the plurality of elastic members, and an insert comprising at least one of a filler material or an elongated coiled member disposed within the hollow tube; and/or wherein at least a portion of the cuff is at least partially disposed on the abluminal surface of the stent when arranged in the second orientation and at least partially positioned outward of the proximal end of the stent when arranged in the first orientation; and/or wherein the cuff is at least partially disposed on the abluminal surface of the stent when the plurality of elastic members are in the first orientation and second orientation.

A stent assembly for use in replacing a native heart valve in accordance with one embodiment of the disclosure is constructed from a stent; a cuff coupled to the stent having a first orientation and a second orientation; and a plurality of members coupled between the stent and cuff, the members configured to arrange the cuff between the first and second orientations, wherein the members remain coupled to the stent and cuff after replacement of the native valve.

In the aforesaid prosthetic heart valve, wherein the stent defines a lumen, and wherein the cuff when arranged in the first orientation is disposed within the lumen, and wherein the cuff when arranged in the second orientation is disposed circumscribing the stent overlying an abluminal surface thereof forming a cuff seal; and/or wherein the inverting members comprise at least one of an elastic member and a coiled member having a tensioned first state and a relaxed second state; and/or wherein the inverting members are in a tensioned state when the cuff is in the first orientation and a relaxed state when the cuff is in the second orientation.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure.

The invention claimed is:

1. A prosthetic heart valve, comprising:
a self-expanding stent having an inflow end, an outflow end, a luminal surface defining a lumen through the stent, and an abluminal surface opposite the luminal surface, the stent having an expanded condition and a collapsed condition, the stent being formed of cells, the cells including a proximal-most row of diamond-shaped cells at the inflow end of the stent;
a plurality of prosthetic leaflets disposed within the lumen of the stent; and
a cuff assembly including a first cuff portion and a second cuff portion,
wherein the first cuff portion is positioned on the luminal surface of the stent in both the expanded condition of the stent and the collapsed condition of the stent;
wherein the second cuff portion is positioned on the abluminal surface of the stent in a deployed configuration of the second cuff portion so that the second cuff covers at least a portion of the proximal-most row of cells, the second cuff portion having a terminal edge that is positioned a spaced distance from the inflow end of the stent and points toward the outflow end of the stent in the deployed configuration of the second cuff portion;
wherein in the deployed condition of the second cuff portion, an entirety of the terminal edge is not directly coupled to the stent so that a continuous pocket is formed between the second cuff portion and the abluminal surface of the stent; and
wherein the first cuff portion is positioned between the plurality of prosthetic leaflets and the stent.

2. The prosthetic heart valve of claim 1, wherein the second cuff portion is formed of a polymer.

3. The prosthetic heart valve of claim 1, wherein the second cuff portion is formed of a fabric.

4. The prosthetic heart valve of claim 1, wherein the second cuff portion is formed of a biological tissue.

5. The prosthetic heart valve of claim 4, wherein the biological tissue is bovine or porcine pericardium.

6. The prosthetic heart valve of claim 1, wherein the second cuff portion has an initial configuration in which the terminal edge of the second cuff portion is positioned a spaced distance from the inflow end of the stent and points away from the outflow end of the stent.

7. The prosthetic heart valve of claim 6, wherein the second cuff portion moves from the initial configuration to the deployed configuration upon movement of the stent from the collapsed condition to the expanded condition.

8. The prosthetic heart valve of claim 7, further comprising a plurality of elongated members each having a first end coupled to the stent and a second end coupled to the second cuff portion, the plurality of elongated members each being formed of shape-memory material.

9. The prosthetic heart valve of claim 8, wherein the elongated members are in a tensioned condition in the initial configuration of the second cuff portion, and are in a relaxed condition in the deployed configuration of the second cuff portion.

10. A method of sealing a prosthetic heart valve against paravalvular leak, the method comprising:
delivering the prosthetic heart valve to a native aortic valve, the prosthetic heart valve including:
a stent having an inflow end, an outflow end, a luminal surface defining a lumen through the stent, and an abluminal surface opposite the luminal surface, the stent having an expanded condition and a collapsed condition, the stent being formed of cells, the cells including a proximal-most row of diamond-shaped cells at the inflow end of the stent;
a plurality of prosthetic leaflets disposed within the lumen of the stent; and
a cuff assembly including a first cuff portion and a second cuff portion;
allowing the prosthetic heart valve to self-expand into the native aortic valve so that (i) the first cuff portion is positioned on the luminal surface of the stent, (ii) the second cuff portion is positioned on the abluminal surface of the stent and covers at least a portion of the proximal-most row of cells, and (iii) the second cuff portion has a terminal edge that is positioned a spaced distance from the inflow end of the stent and points toward the outflow end of the stent, an entirety of the terminal edge being not directly coupled to the stent; and
allowing blood to be received within a continuous pocket formed between the second cuff portion and the abluminal surface of the stent,
wherein the first cuff portion is positioned between the plurality of prosthetic leaflets and the stent.

11. The method of claim 10, wherein upon blood being received within the continuous pocket, the continuous pocket expands and seals around calcified nodules of the native aortic valve.

12. The method of claim 10, wherein the second cuff portion is formed of a polymer.

13. The method of claim 10, wherein the second cuff portion is formed of a fabric.

14. The method of claim 10, wherein the second cuff portion is formed of a biological tissue.

15. The method of claim 14, wherein the biological tissue is bovine or porcine pericardium.

16. The method of claim 10, wherein the second cuff portion has an initial configuration in which the terminal edge of the second cuff portion is positioned a spaced distance from the inflow end of the stent and points away from the outflow end of the stent, the second cuff portion being in the initial condition when delivering the prosthetic heart valve.

17. The method of claim 16, wherein the second cuff portion moves from the initial configuration to a deployed configuration, in which the terminal edge points toward the outflow end of the stent, upon allowing the prosthetic heart valve to self-expand into the native aortic valve.

\* \* \* \* \*